(12) United States Patent
Peng et al.

(10) Patent No.: US 11,390,574 B2
(45) Date of Patent: Jul. 19, 2022

(54) PROCESS FOR PRODUCING 1,1,3-TRICHLORO-4,4,4-TRIFLUOROBUT-1-ENE

(71) Applicant: THE CHEMOURS COMPANY FC, LLC, Wilmington, DE (US)

(72) Inventors: Sheng Peng, Hockessin, DE (US); Viacheslav A. Petrov, Hockessin, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 180 days.

(21) Appl. No.: 16/769,949

(22) PCT Filed: Dec. 4, 2018

(86) PCT No.: PCT/US2018/063825
§ 371 (c)(1),
(2) Date: Jun. 4, 2020

(87) PCT Pub. No.: WO2019/113052
PCT Pub. Date: Jun. 13, 2019

(65) Prior Publication Data
US 2021/0188743 A1    Jun. 24, 2021

Related U.S. Application Data

(60) Provisional application No. 62/594,383, filed on Dec. 4, 2017.

(51) Int. Cl.

| | | |
|---|---|---|
| C09K 17/20 | (2006.01) | |
| C09K 5/04 | (2006.01) | |
| C11D 3/24 | (2006.01) | |
| A62D 1/00 | (2006.01) | |
| C08J 9/14 | (2006.01) | |
| C09K 3/14 | (2006.01) | |
| C07C 17/20 | (2006.01) | |
| C06B 49/00 | (2006.01) | |

(52) U.S. Cl.
CPC ............. *C07C 17/20* (2013.01); *A62D 1/00* (2013.01); *C06B 49/00* (2013.01); *C08J 9/144* (2013.01); *C09K 3/14* (2013.01); *C09K 5/044* (2013.01); *C11D 3/245* (2013.01); *C09K 2205/22* (2013.01)

(58) Field of Classification Search
None
See application file for complete search history.

(56) References Cited

U.S. PATENT DOCUMENTS

| | | | |
|---|---|---|---|
| 8,461,401 B2 | 6/2013 | Wang | |
| 2007/0152200 A1* | 7/2007 | Hedrick | A62D 1/00 252/601 |
| 2011/0237844 A1* | 9/2011 | Tung | C07C 17/278 570/151 |
| 2012/0175137 A1 | 7/2012 | Hedrick | |
| 2017/0015607 A1* | 1/2017 | Baldychev | C07C 17/354 |
| 2018/0215690 A1* | 8/2018 | Nappa | B01J 27/12 |
| 2019/0077733 A1* | 3/2019 | Peng | B01J 31/0239 |

OTHER PUBLICATIONS

International Search Report for PCT/US2018/063825 dated Mar. 6, 2019, 18 pages.

* cited by examiner

*Primary Examiner* — Joseph D Anthony

(57) ABSTRACT

The present application provides processes and intermediates for preparing (E)-1,1,1,4,4,4-hexafluoro-2-butene and compositions which may be useful in applications including refrigerants, high-temperature heat pumps, organic Rankine cycles, as fire extinguishing/fire suppression agents, propellants, foam blowing agents, solvents, and/or cleaning fluids.

13 Claims, No Drawings

PROCESS FOR PRODUCING 1,1,3-TRICHLORO-4,4,4-TRIFLUOROBUT-1-ENE

CROSS REFERENCE TO RELATED APPLICATIONS

This application is a national filing under 35 U.S.C. 371 of International Application No. PCT/US2018/063825 filed Dec. 4, 2018, and claims priority of U.S. Provisional Application No. 62/594,383 filed Dec. 4, 2017, the disclosures of which are incorporated herein by reference in its entirety.

TECHNICAL FIELD

This invention relates to processes and intermediates for preparing (E)-1,1,1,4,4,4-hexafluoro-2-butene and compositions which may be useful in applications including refrigerants, high-temperature heat pumps, organic Rankine cycles, as fire extinguishing/fire suppression agents, propellants, foam blowing agents, solvents, and/or cleaning fluids.

BACKGROUND

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

SUMMARY

The present application provides, inter alia, a process of preparing 1,1,3-trichloro-4,4,4-trifluorobut-1-ene, which is a key intermediate in the preparation of (E)-1,1,1,4,4,4-hexafluorobut-2-ene. The processes for preparing the 1,1,3-trichloro-4,4,4-trifluorobut-1-ene comprise heating 2,4,4,4-tetrachloro-1,1,1-trifluorobutane in the presence of a transition metal catalyst to form the 1,1,3-trichloro-4,4,4-trifluorobut-1-ene, and substantially isolating the 1,1,3-trichloro-4,4,4-trifluorobut-1-ene.

The present application further provides processes for preparing (E)-1,1,1,4,4,4-hexafluorobut-2-ene using the 1,1,3-trichloro-4,4,4-trifluorobut-1-ene described herein.

The present application further provides compositions prepared according to one or more of the processes described herein.

The present application further provides the use of compositions of the invention in applications including refrigeration (e.g., as refrigerant compositions), high-temperature heat pumps, organic Rankine cycles, fire extinguishing/fire suppression agents, propellants, foam blowing agents, solvents, and/or cleaning fluids.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for compositions that do not contribute to the destruction of stratospheric ozone and also have low global warming potentials (GWPs). Certain hydrofluoroolefins, such as 1,1,1,4,4,4-hexafluoro-2-butene ($CF_3CH=CHCF_3$, HFO-1336mzz), meets both goals. For example, (E)-HFO-1336mzz (i.e., (E)-1,1,1,4,4,4-hexafluoro-2-butene) is useful in many applications (e.g., a foam expansion agent or refrigerant) due to its low GWP, non-flammability, high efficiency, and thermal stability. The present application describes key intermediates useful in preparing (E)-1,1,1,4,4-hexafluoro-2-butene, processes for preparing said intermediates, and integrated processes for preparing the intermediates

Definitions

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

As used herein, the term "about" is meant to account for variations due to experimental error (e.g., plus or minus approximately 10% of the indicated value). All measurements reported herein are understood to be modified by the term "about", whether or not the term is explicitly used, unless explicitly stated otherwise.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Global warming potential (GWP) is an index for estimating relative global warming contribution due to atmospheric emission of a kilogram of a particular greenhouse gas compared to emission of a kilogram of carbon dioxide. GWP can be calculated for different time horizons showing the effect of atmospheric lifetime for a given gas. The GWP for the 100-year time horizon is commonly the value referenced.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl" refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group has 1 to 6, 1 to 4, 1 to 3, or 1 to 2 carbon atoms.

As used herein, "halide" refers to fluoride, chloride, bromide, or iodide. In some embodiments, the halo is chloride or bromide.

As used herein, "tri($C_{n-m}$ alkyl)phosphate" refers to a compound of formula $P(O)O(C_{n-m}$ alkyl$)_3$, wherein each $C_{n-m}$ alkyl refers to a saturated hydrocarbon group that may be straight-chain or branched, having n to m carbons, and wherein each $C_{n-m}$ alkyl group may be the same or different. Exemplary tri($C_{n-m}$ alkyl)phosphates include, but are not limited to, trimethylphosphate, triethylphosphate, tributylphosphate, dimethylethylphosphate, dimethylbutylphosphate, butylethylmethylphosphate, and the like.

As used herein, "alkali metal hydroxide base" refers to a compound of formula MOH, wherein M is an alkali metal (e.g. sodium, potassium, and the like).

As used herein, the term "substantially isolated" is meant that the compound or composition is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein. Methods for isolating compounds and compositions are routine in the art.

As used herein, "transition metal oxide" refers to a compound of formula $M_2O_y$, wherein M is a transition metal (e.g., chromium, iron, and the like) and y is the oxidation number of the transition metal. Exemplary transition metal oxides include, but are not limited to, chromium (III) oxide ($Cr_2O_3$), iron (II) oxide (FeO), iron (III) oxide ($Fe_2O_3$), and the like. The transition metal oxide may be optionally supported on a substrate, such as activated carbon, alumina, and fluorinated alumina. Additional transition metal oxide catalysts and support substrates may be found, for example, in U.S. Pat. No. 8,461,401, the disclosure of which is incorporated herein by reference in its entirety.

As used herein, "transition metal halide" refers to a compound of formula $MX_y$, wherein M is a transition metal (e.g., chromium, iron, and the like), X is a halide, (e.g., fluoride, chloride, and the like) and y is the oxidation number of the transition metal. Exemplary transition metal halides include, but are not limited to, iron (III) chloride ($FeCl_3$), titanium (IV) chloride ($TiCl_4$), and the like. Additional transition metal halides may be found, for example, in U.S. Pat. No. 8,461,401, the disclosure of which is incorporated herein by reference in its entirety.

As used herein, "absence of HF" means that a constant flow of HF is not present during the reaction, but not does exclude use of HF to activate the catalyst prior to the reaction.

The compounds described herein can be asymmetric (e.g., having one or more stereocenters). All stereoisomers, such as enantiomers and diastereomers, are intended unless otherwise indicated. Cis/trans and/or E/Z geometric isomers of the compounds of the present invention are described and may be isolated as a mixture of isomers or as separated isomeric forms.

Chemicals, Abbreviations, and Acronyms

| ID | Chemical Name |
|---|---|
| R-123 or HFC-123 | 2,2-dichloro-1,1,1-trifluoroethane |
| R-11 or CFC-11 | trichlorofluoromethane |
| R-245fa or HFC-245fa | 1,1,1,3,3-pentafluoropropane |
| R-114 or CFC-114 | 1,2-dichloro-1,1,2,2-tetrafluoroethane |
| R-236fa or HFC-236fa | 1,1,1,3,3,3-hexafluoropropane |
| R-236ea or HFC-236ea | 1,1,1,2,3,3-hexafluoropropane |
| R-124 or HCFC-124 | 2-chloro-1,1,1,2-tetrafluoroethane |
| 343jfd | 2,4,4,4-tetrachloro-1,1,1-trifluorobutane |
| 1336mzz or HFO-1336mzz | 1,1,1,4,4,4-hexafluorobut-2-ene |
| E-1336mzz or (E)-HFO-1336mzz | (E)-1,1,1,4,4,4-hexafluorobut-2-ene |
| Z-1336mzz or (Z)-HFO-1336mzz | (Z)-1,1,1,4,4,4-hexafluorobut-2-ene |
| 1333azd | 1,1,3-trichloro-4,4,4-trifluorobut-1-ene |
| 1336mt | 3,3,3-trifluoro-2-(trifluoromethyl)prop-1-ene |
| 346mdf | 2-chloro-1,1,1,4,4,4-hexafluorobutane |
| 1335lzz | 1-chloro-1,1,4,4,4-pentafluorobut-2-ene |
| 356mff | 1,1,1,4,4,4-hexafluorobutane |
| 1326mxz | 2-chloro-1,1,1,4,4,4-hexafluoro-2-butene |
| 356jff | $CCl_3CH_2CH_2CF_3$ |
| 343jmz | 1,1,1-trichloro-2-(chloromethyl)-3,3,3-trifluoropropane |
| CFC | chlorofluorocarbon |
| HCFC | hydrochlorofluorocarbon |
| HFC | hydrofluorocarbons |
| HFO | hydrofluoroolefin |
| GWP | global warming potential |
| POE | polyol ester |
| PAG | polyalkylene glycol |
| PVE | polyvinyl ether |
| PFPE | perfluoropolyether |

Processes

The present application provides a process of preparing 1,1,3-trichloro-4,4,4-trifluorobut-1-ene (e.g., a vapor phase process or a liquid phase process). In some embodiments, the process comprises heating 2,4,4,4-tetrachloro-1,1,1-trifluorobutane in the presence of a metal catalyst (e.g., a first metal catalyst) to form the 1,1,3-trichloro-4,4,4-trifluorobut-1-ene.

In some embodiments, the process of preparing the 1,1,3-trichloro-4,4,4-trifluorobut-1-ene is performed in the absence of hydrogen fluoride (F).

In some embodiments, the process further comprises substantially isolating the 1,1,3-trichloro-4,4,4-trifluorobut-1-ene. In some embodiments, the 1,1,3-trichloro-4,4,4-trifluorobut-1-ene is substantially isolated by distillation.

Exemplary metal catalysts useful in the process of preparing 1,1,3-trichloro-4,4,4-trifluorobut-1-ene include, but are not limited to, transition metal halides (e.g., Group IVb metal halides, Group Vb metal halides), transition metal oxides (e.g., chromium oxide), Group IIIa metal halides (e.g., aluminum halides such as aluminum chloride or aluminum fluoride), and combinations thereof. In some embodiments, the metal catalyst is selected from the group consisting of an antimony halide (e.g., $SbCl_5$, $SbCl_3$, $SbF_5$), a tin halide (e.g., $SnCl_4$), a tantalum halide (e.g., $TaCl_5$), a titanium halide (e.g., $TiCl_4$), a niobium halide (e.g., $NbCl_5$), a molybdenum halide (e.g., $MoCl_6$), an iron halide (e.g., $FeCl_3$), chrome halide (e.g. chrome chloride), a chrome oxide, an aluminum halide (e.g., aluminum chloride or aluminum fluoride), an alumina halide (e.g., alumina fluoride), a fluorinated chrome halide, a fluorinated chrome oxide, a fluorinated aluminum halide, a fluorinated aluminum oxide, or any combination thereof. Additional metal catalysts may be found, for example, in U.S. Pat. No. 8,461,401, the disclosure of which is incorporated herein by reference in its entirety.

In some embodiments, the metal catalyst is a transition metal catalyst. In some embodiments, the transition metal catalyst is a transition metal oxide catalyst or a transition metal halide catalyst. In some embodiments, the transition metal catalyst is selected from chromium oxide, chromium chloride, and iron (III) chloride. In some embodiments, the transition metal catalyst is supported on a substrate (e.g., carbon).

In some embodiments, the transition metal catalyst is a transition metal oxide catalyst. In some embodiments, the transition metal oxide catalyst is supported on a substrate. In some embodiments, the transition metal oxide catalyst is chromium oxide. In some embodiments, the chromium oxide is supported on a substrate. In some embodiments, the transition metal oxide catalyst is chromium (III) oxide. In some embodiments, transition metal oxide catalyst is chromium (III) oxide on carbon.

In some embodiments, the transition metal catalyst is a transition metal halide catalyst. In some embodiments, the transition metal halide is supported on a substrate. In some embodiments, the metal halide catalyst is an iron halide catalyst. In some embodiments, the metal halide catalyst is a chromium halide catalyst. In some embodiments, the metal halide catalyst is iron (III) chloride. In some embodiments, the metal halide catalyst is chromium chloride. In some embodiments, the metal halide catalyst is chromium chloride on carbon.

In some embodiments, the process of preparing the 1,1,3-trichloro-4,4,4-trifluorobut-1-ene comprises contacting the metal catalyst with hydrogen fluoride to form an activated metal catalyst (e.g., a partially or fully fluorinated metal catalyst). In some embodiments, the activated metal catalyst is prepared prior to heating the 2,4,4,4-tetrachloro-1,1,1-trifluorobutane in the presence of the metal catalyst.

In some embodiments, the process of preparing the 1,1,3-trichloro-4,4,4-trifluorobut-1-ene further comprises contacting chromium (III) oxide on carbon with hydrogen fluoride to form an activated chromium (III) oxide on carbon catalyst prior to heating the 2,4,4,4-tetrachloro-1,1,1-trifluorobutane in the presence of the chromium (III) oxide on carbon catalyst.

In some embodiments, the process of preparing the activated metal catalyst is performed at a temperature of from about 30° C. to about 350° C., for example, about 30° C. to about 300° C., about 30° C. to about 250° C., about 30° C. to about 200° C., about 30° C. to about 100° C., about 100° C. to about 350° C., about 100° C. to about 300° C., about 100° C. to about 250° C., about 100° C. to about 200° C., about 200° C. to about 350° C., about 200° C. to about 300° C., about 200° C. to about 250° C., about 250° C. to about 350° C., about 250° C. to about 300° C., or about 300° C. to about 350° C. In some embodiments, the contacting of the metal catalyst with the hydrogen fluoride is performed at a temperature of from about 280° C. to about 320° C.

In some embodiments, the process of preparing the 1,1,3-trichloro-4,4,4-trifluorobut-1-ene is performed as a vapor phase process. In some embodiments, the vapor phase process of preparing the 1,1,3-trichloro-4,4,4-trifluorobut-1-ene is performed in the absence of an additional solvent component.

In some embodiments, the process of preparing the 1,1,3-trichloro-4,4,4-trifluorobut-1-ene is performed as a vapor phase process at a temperature of from about 100° C. to about 500° C., for example, about 100° C. to about 400° C., about 100° C. to about 300° C., about 100° C. to about 200° C., about 200° C. to about 500° C., about 200° C. to about 400° C., about 200° C. to about 300° C., about 300° C. to about 500° C., about 300° C. to about 400° C., or about 400° C. to about 500° C. In some embodiments, the process of preparing the 1,1,3-trichloro-4,4,4-trifluorobut-1-ene is performed as a vapor phase process at a temperature of from about 150° C. to about 200° C.

In some embodiments, the process of preparing the 1,1,3-trichloro-4,4,4-trifluorobut-1-ene is performed as a liquid phase process. In some embodiments, the liquid phase process of preparing the 1,1,3-trichloro-4,4,4-trifluorobut-1-ene is performed in the absence of an additional solvent component.

In some embodiments, the process of preparing the 1,1,3-trichloro-4,4,4-trifluorobut-1-ene is performed as a liquid phase process at a temperature of from about 30° C. to about 200° C., for example, about 30° C. to about 150° C., about 30° C. to about 120° C., about 30° C. to about 75° C., about 75° C. to about 200° C., about 75° C. to about 150° C., about 75° C. to about 120° C., about 120° C. to about 200° C., about 120° C. to about 150° C., or about 150° C. to about 200° C. In some embodiments, the process of preparing the 1,1,3-trichloro-4,4,4-trifluorobut-1-ene is performed as a liquid phase process at a temperature of from about 75° C. to about 115° C.

In some embodiments, the process of preparing the 1,1,3-trichloro-4,4,4-trifluorobut-1-ene is performed at a pressure of from about 0 psig to about 200 psig, for example, about 0 psig to about 150 psig, about 0 psig to about 100 psig, about 0 psig to about 50 psig, about 50 psig to about 200 psig, about 50 psig to about 150 psig, about 50 psig to about 100 psig, about 100 psig to about 200 psig, about 100 psig to about 150 psig, or about 150 psig to about 200 psig. In some embodiments, the process of preparing the 1,1,3-trichloro-4,4,4-trifluorobut-1-ene is performed at a pressure of from about 0 psig to about 150 psig.

The present application further provides a process of preparing 1,1,3-trichloro-4,4,4-trifluorobut-1-ene, comprising heating 2,4,4,4-tetrachloro-1,1,1-trifluorobutane in the presence of a base to form the 1,1,3-trichloro-4,4,4-trifluorobut-1-ene. In some embodiments, the process of heating the 2,4,4,4-tetrachloro-1,1,1-trifluorobutane in the presence of a base is performed as liquid phase process. In some embodiments, the process of heating the 2,4,4,4-tetrachloro-1,1,1-trifluorobutane in the presence of a base is performed in an aqueous solvent.

In some embodiments, the process further comprises substantially isolating the 1,1,3-trichloro-4,4,4-trifluorobut-1-ene. In some embodiments, the 1,1,3-trichloro-4,4,4-trifluorobut-1-ene is substantially isolated by distillation.

Exemplary bases include, but are not limited to, lithium hydroxide, sodium hydroxide, potassium hydroxide, lithium carbonate, sodium carbonate, potassium carbonate, and sodium bicarbonate, each of which may optionally be prepared in water to form an aqueous base mixture or aqueous base solution. In some embodiments, the base is an aqueous base.

In some embodiments, the aqueous base is an aqueous alkali metal hydroxide base.

In some embodiments, the aqueous base is aqueous sodium hydroxide or aqueous potassium hydroxide.

In some embodiments, the present application provides a vapor phase process of preparing 1,1,3-trichloro-4,4,4-trifluorobut-1-ene, comprising:

i) contacting chromium (III) oxide on carbon with hydrogen fluoride at a temperature of from about 280° C. to about 320° C. to form an activated chromium (III) oxide on carbon catalyst; and ii) heating 2,4,4,4-tetrachloro-1,1,1-trifluorobutane in the presence of the activated chromium (III) oxide on carbon catalyst at a temperature of from about 150° C. to about 200° C. and at a pressure of from about 0 psig to 150 psig to form the 1,1,3-trichloro-4,4,4-trifluorobut-1-ene.

In some embodiments, the vapor phase process further comprises substantially isolating the 1,1,3-trichloro-4,4,4-trifluorobut-1-ene.

In some embodiments, the heating of step ii) of the vapor phase process is performed in the absence of hydrogen fluoride.

In some embodiments, the present application provides a liquid phase process of preparing 1,1,3-trichloro-4,4,4-trifluorobut-1-ene, comprising:

i) heating 2,4,4,4-tetrachloro-1,1,1-trifluorobutane in the presence of iron (III) chloride at a temperature of from about 75° C. to about 115° C. to form the 1,1,3-trichloro-4,4,4-trifluorobut-1-ene.

In some embodiments, the liquid phase process further comprises substantially isolating the 1,1,3-trichloro-4,4,4-trifluorobut-1-ene.

In some embodiments, the 1,1,3-trichloro-4,4,4-trifluorobut-1-ene prepared according to a process described herein is substantially isolated in greater than about 75% yield, greater than about 85% yield, greater than about 90% yield, greater than about 95% yield, greater than about 97% yield, greater than about 99% yield, or greater than about 99.5% yield.

In some embodiments, the 1,1,3-trichloro-4,4,4-trifluorobut-1-ene prepared according to a process described herein is substantially isolated in greater than about 75% purity, greater than about 85% purity, greater than about 90% purity, greater than about 95% purity, greater than about 97% purity, greater than about 99% purity, or greater than about 99.5% purity.

The present application further provides a process comprising heating 1,1,3-trichloro-4,4,4-trifluorobut-1-ene (e.g., the substantially isolated 1,1,3-trichloro-4,4,4-trifluorobut-1-ene prepared according to a process described herein) in the presence of a metal catalyst (e.g., a second metal catalyst) to form (E)-1,1,1,4,4,4-hexafluorobut-2-ene.

Exemplary metal catalysts useful in the process of preparing (E)-1,1,1,4,4,4-hexafluorobut-2-ene include, but are not limited to, metal halides, halogenated metal oxides, neutral (or zero oxidation state) metal or metal alloy, or activated carbon in bulk or supported form. Additional exemplary metal catalysts useful for preparing (E)-1,1,1,4,4,4-hexafluorobut-2-ene may be found, for example, in U.S. Pat. No. 8,461,401 and U.S. patent application Ser. No. 15/124,738, the disclosures of each of which are incorporated herein by reference in their entireties.

In some embodiments, the metal catalyst (e.g., the second metal catalyst) useful in the process of preparing (E)-1,1,1,4,4,4-hexafluorobut-2-ene is a transition metal catalyst (e.g., a second transition metal catalyst). In some embodiments, the transition metal catalyst is a transition metal oxide catalyst. In some embodiments, the transition metal oxide catalyst is supported on a substrate. In some embodiments, the transition metal oxide catalyst is chromium oxide. In some embodiments, the chromium oxide is supported on a substrate. In some embodiments, the transition metal oxide catalyst is chromium (III) oxide. In some embodiments, transition metal oxide catalyst is chromium (III) oxide on carbon.

In some embodiments, the 2,4,4,4-tetrachloro-1,1,1-trifluorobutane described herein is prepared by a process comprising reacting 3,3,3-trifluoroprop-1-ene with carbon tetrachloride in the presence of a metal catalyst (e.g., a third transition metal catalyst) and a tri($C_{1-6}$ alkyl) phosphate.

In some embodiments, the transition metal catalyst useful in preparing 2,4,4,4-tetrachloro-1,1,1-trifluorobutane is iron powder.

In some embodiments, the tri($C_{1-6}$ alkyl)phosphate is tributyl phosphate.

Additional processes and conditions for preparing 2,4,4,4-tetrachloro-1,1,1-trifluorobutane may be found, for example, in U.S. Pat. No. 8,461,401 and U.S. patent application Ser. No. 15/124,738, the disclosures of each of which are incorporated herein by reference in their entireties.

The processes and chemical reactions described herein can be monitored according to any suitable method known in the art. For example, product formation can be monitored by spectroscopic means, such as nuclear magnetic resonance spectroscopy (e.g., $^1$H or $^{13}$C), infrared spectroscopy, mass spectrometry, or by chromatographic methods such as high performance liquid chromatography (HPLC) or liquid chromatography-mass spectroscopy (LCMS). Compounds can be purified by those skilled in the art by a variety of methods including, but not limited to, high performance liquid chromatography (HPLC) or distillation.

Compositions

The present application further provides compositions prepared according to one or more of the processes described herein. In some embodiments, the compositions of the invention are substantially isolated.

In some embodiments, the compositions of the invention comprise a major component (e.g., (E)-1,1,1,4,4,4-hexafluorobut-2-ene or 2,4,4,4-tetrachloro-1,1,1-trifluorobutane) in combination with one or more minor components (i.e., additional compounds or addition components). In some embodiments, the compositions of the invention are prepared according to one or more of the processes described herein. In some embodiments, the major component of the composition comprises greater than about 50 mole percent, greater than about 75 mole percent, greater than about 85 mole percent, greater than about 90 mole percent, greater than about 95 mole percent, greater than about 97 mole percent, greater than about 99 mole percent, or greater than about 99.5 mole percent of the composition.

The minor components of the compositions described herein may provide, for example, improved solubility for active ingredients (e.g., the major component of the composition) in an aerosol or polymer constituents of a foam. Additionally, for refrigerant applications, such as use in air conditioning, heat pumps, refrigeration, and power cycles (e.g., organic Rankine cycles), the minor components of the compositions may provide improved solubility with refrigeration lubricants, such as mineral oils, alkylbenzenes, synthetic paraffins, synthetic naphthenes, poly(alpha)olefins, polyol esters (POE), polyalkylene glycols (PAG), polyvinyl ethers (PVE), or perfluoropolyethers (PFPE), or mixtures thereof.

Further, the presence of the minor compounds in a sample of a composition of the invention may be used to identify the process by which the compound was manufactured.

In some embodiments, the present application provides a composition comprising:
(E)-1,1,1,4,4,4-hexafluorobut-2-ene;
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene.

In some embodiments, the composition comprises a major component which is (E)-1,1,1,4,4,4-hexafluorobut-2-ene in combination with one or more of the following minor components:
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene.

In some embodiments, the composition comprises a major component which is (E)-1,1,1,4,4,4-hexafluorobut-2-ene in combination with the following minor components:
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene.

In some embodiments, the composition comprises greater than about 90 mole percent (E)-1,1,1,4,4,4-hexafluorobut-2-ene.

In some embodiments, the composition comprises greater than about 97 mole percent (E)-1,1,1,4,4,4-hexafluorobut-2-ene.

In some embodiments, the composition comprises greater than about 99 mole percent (E)-1,1,1,4,4,4-hexafluorobut-2-ene.

In some embodiments, the composition comprising a major component which is (E)-1,1,1,4,4,4-hexafluorobut-2-ene is prepared according to one or more of the processes described herein.

In some embodiments, the present application provides a composition, comprising:
(E)-1,1,1,4,4,4-hexafluorobut-2-ene;
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene.
which is prepared according to a process comprising heating 2,4,4,4-tetrachloro-1,1,1-trifluorobutane in the presence of a metal catalyst to form the composition, wherein the metal catalyst is defined according to the definition provided herein for the processes of the invention.

In some embodiments, the composition comprises a major component which is (E)-1,1,1,4,4,4-hexafluorobut-2-ene in combination with one or more of following minor components:
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene;
wherein the composition is prepared according to a process comprising:
i) heating 2,4,4,4-tetrachloro-1,1,1-trifluorobutane in the presence of a first metal catalyst to form a first mixture comprising 1,1,3-trichloro-4,4,4-trifluorobut-1-ene; and
ii) heating the 1,1,3-trichloro-4,4,4-trifluorobut-1-ene in the presence of a second metal catalyst to form the composition;
wherein the metal catalysts are defined according to the definitions provided herein for the processes of the invention.

In some embodiments, the composition comprises a major component which is (E)-1,1,1,4,4,4-hexafluorobut-2-ene in combination with the following minor components:
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene;
wherein the composition is prepared according to a process comprising:
i) heating 2,4,4,4-tetrachloro-1,1,1-trifluorobutane in the presence of a first metal catalyst to form a first mixture comprising 1,1,3-trichloro-4,4,4-trifluorobut-1-ene; and
ii) heating the 1,1,3-trichloro-4,4,4-trifluorobut-1-ene in the presence of a second metal catalyst to form the composition;
wherein the metal catalysts are defined according to the definitions provided herein for the processes of the invention.

In some embodiments, the 1,1,3-trichloro-4,4,4-trifluorobut-1-ene is substantially isolated prior to the heating of step ii).

In some embodiments, the composition comprising a major component which is (E)-1,1,1,4,4,4-hexafluorobut-2-ene is substantially isolated.

In some embodiments, the present application provides a composition comprising:
2,4,4,4-tetrachloro-1,1,1-trifluorobutane;
1,1,1-trichloro-4,4,4-trifluorobutane; and
1,1,1-trichloro-2-(chloromethyl)-3,3,3-trifluoropropane.

In some embodiments, the composition comprises a major component which is 2,4,4,4-tetrachloro-1,1,1-trifluorobutane in combination with one or more of the following minor components:
1,1,1-trichloro-4,4,4-trifluorobutane; and
1,1,1-trichloro-2-(chloromethyl)-3,3,3-trifluoropropane.

In some embodiments, the composition comprises a major component which is 2,4,4,4-tetrachloro-1,1,1-trifluorobutane in combination with the following minor components:
1,1,1-trichloro-4,4,4-trifluorobutane; and
1,1,1-trichloro-2-(chloromethyl)-3,3,3-trifluoropropane.

In some embodiments, the composition comprises greater than about 90 mole percent 2,4,4,4-tetrachloro-1,1,1-trifluorobutane.

In some embodiments, the composition comprises greater than about 97 mole percent 2,4,4,4-tetrachloro-1,1,1-trifluorobutane.

In some embodiments, the composition comprises greater than about 99 mole percent 2,4,4,4-tetrachloro-1,1,1-trifluorobutane.

In some embodiments, the composition comprising a major component which is 2,4,4,4-tetrachloro-1,1,1-trifluorobutane is prepared according to one or more of the processes described herein.

In some embodiments, the composition comprises a major component which is 2,4,4,4-tetrachloro-1,1,1-trifluorobutane in combination with the following minor components: 1,1,1-trichloro-4,4,4-trifluorobutane; and 1,1,1-trichloro-2-(chloromethyl)-3,3,3-trifluoropropane; wherein the composition is prepared according to a process comprising:

i) reacting 3,3,3-trifluoroprop-1-ene with carbon tetrachloride in the presence of a metal catalyst and a tri($C_{1-6}$ alkyl) phosphate in the presence of a transition metal catalyst to form the composition, wherein the metal catalyst and tri($C_{1-6}$ alkyl)phosphate are defined according to the definitions provided herein for the processes of the invention.

In some embodiments, the composition comprising a major component which is 2,4,4,4-tetrachloro-1,1,1-trifluorobutane is substantially isolated.

METHODS OF USE

The composition provided herein (i.e., the compositions of the invention) may be useful, for example, in a wide range of applications, including their use as refrigerants, uses in high-temperature heat pumps, organic Rankine cycles, as fire extinguishing/fire suppression agents, propellants, foam blowing agents, solvents, and/or cleaning fluids.

In some embodiments, minor components of the compositions containing at least one chlorine atom may provide improved solubility for the major component of the composition (e.g., (E)-1,1,1,4,4,4-hexafluorobut-2-ene or 2,4,4,4-tetrachloro-1,1,1-trifluorobutane) in an aerosol or polymer constituents of a foam.

For example, unsaturated fluorocarbons, such as (E)-1,1,1,4,4,4-hexafluoro-2-butene, exhibit different solubility than other fluorocarbon propellants. This reduced solubility can make it difficult to prepare single phase aqueous homogenous aerosol formulations. The presence of low level chlorinated impurities can improve mixing and ease formulations and use of aerosol products.

Unsaturated fluorocarbons, such as (E)-1,1,1,4,4,4-hexafluorobut-2-ene, also exhibit different solubility than other common blowing agents. The reduced solubility can assist in seeding small cell growth during a foaming reaction but the compounds can be difficult to mix. The presence of low level chlorinated impurities can improve mixing and foam processing performance without sacrificing the benefits from the lower HFO solubility. Also, the chlorinated compounds typically have lower vapor thermal conductivities and so will impart improved insulating performance to a foam insulation product.

Additionally, for refrigerant applications, such as use in air conditioning, heat pumps, refrigeration, and power cycles (e.g., organic Rankine cycles), minor components of the compositions of the invention containing at least one chlorine atom may provide improved solubility with refrigeration lubricants, such as mineral oils, alkylbenzenes, synthetic paraffins, synthetic naphthenes, poly(alpha)olefins, polyol esters (POE), polyalkylene glycols (PAG), polyvinyl ethers (PVE), or perfluoropolyethers (PFPE) or mixtures thereof.

Further, the minor components of the compositions of the invention may assist in improving leak detection ability. Leakage of refrigerants may lead to loss of refrigerant from a system, thus increasing cost of operation due to the need to top-off refrigerant charge, and even minor loss of refrigerant from a system may impact proper operation. Finally, leakage of refrigerant may lead to excessive environmental contamination. In particular, chlorinated compounds, even at low levels can increase the detectability of refrigerant at the point of a leak. Thus, the system may be repaired or redesigned to prevent refrigerant leakage.

The levels of minor components in the compositions (e.g., minor components which are chlorinated compounds) must be kept low, however, because higher levels of the minor components may create compatibility problems with materials of construction. In aerosols, these compatibility problems may be with an aerosol container (e.g., cans) or with plastic valve parts. In foams, these compatibility problems may be with equipment seals and gaskets. Additionally, in aerosol products interaction of higher levels of the minor components (e.g., minor components which are chlorinated compounds) may cause instability of the formulation. For example, in foam products, higher levels of chlorinated compounds may soften the foam resulting in dimensional instability and poor strength of the foam.

The compositions described herein may also useful as low global warming potential (GWP) heat transfer compositions, refrigerants, power cycle working fluids, aerosol propellants, foaming agents, blowing agents, solvents, cleaning agents, carrier fluids, displacement drying agents, buffing abrasion agents, polymerization media, expansion agents for poly-olefins and polyurethane, gaseous dielectrics, fire extinguishing agents, and fire suppression agents, in liquid or gaseous form. In some embodiments, the compositions provided herein may be useful as a working fluid used to carry heat from a heat source to a heat sink. Such heat transfer compositions may also be useful as a refrigerant in a cycle wherein the fluid undergoes a phase change (e.g., from a liquid to a gas and back or vice versa).

Examples of heat transfer systems include but are not limited to air conditioners, freezers, refrigerators, heat pumps, water chillers, flooded evaporator chillers, direct expansion chillers, walk-in coolers, heat pumps, mobile refrigerators, mobile air conditioning units and combinations thereof.

In some embodiments, the compositions provided herein may be useful in mobile heat transfer systems, including refrigeration, air conditioning, or heat pump systems or apparatus. In some embodiments, the compositions may be useful in stationary heat transfer systems, including refrigeration, air conditioning, or heat pump systems or apparatus.

As used herein, mobile heat transfer systems refers to any refrigeration, air conditioner, or heating apparatus incorporated into a transportation unit for the road, rail, sea or air. In addition, mobile refrigeration or air conditioner units, include those apparatus that are independent of any moving carrier and are known as "intermodal" systems. Such intermodal systems include "containers' (combined sea/land transport) as well as "swap bodies" (combined road/rail transport).

As used herein, stationary heat transfer systems are systems that are fixed in place during operation. A stationary heat transfer system may be associated within or attached to buildings of any variety or may be stand-alone devices located out of doors, such as a soft drink vending machine. These stationary applications may be stationary air conditioning and heat pumps (including but not limited to chillers, high temperature heat pumps, including trans-critical heat pumps (e.g., with condenser temperatures above 50° C., above 70° C., above 80° C., above 100° C., above 120° C., above 140° C., above 160° C., above 180° C., or above 200° C.), residential, commercial or industrial air conditioning systems, and including window, ductless, ducted, packaged terminal, chillers, and those exterior but connected to the building such as rooftop systems). In stationary refrigeration applications, the compositions provided herein may be useful in high temperature, medium temperature, and/or low temperature refrigeration equipment including commercial, industrial or residential refrigerators and freezers, ice machines, self-contained coolers and freezers, flooded evaporator chillers, direct expansion chillers, walk-in and reach-in coolers and freezers, and combination systems. In some embodiments, the disclosed compositions may be used in supermarket refrigerator systems.

Therefore, in accordance with the present invention, the compositions provided herein may be useful in methods for producing cooling, producing heating, and transferring heat.

In some embodiments, the present application provides a method for producing cooling comprising evaporating a composition provided herein in the vicinity of a body to be cooled, and thereafter condensing said composition.

In some embodiments, the present application provides a method for producing heating comprising condensing a composition provided herein in the vicinity of a body to be heated, and thereafter evaporating said compositions.

In some embodiments, the present application provides a method of using compositions provided herein as heat transfer fluid compositions. In some embodiments, the method comprises transporting said composition from a heat source to a heat sink.

The compositions provided herein may also be useful as low global warming potential (GWP) replacements for currently used refrigerants, including but not limited to, R-123 (i.e., HFC-123, 2,2-dichloro-1,1,1-trifluoroethane), R-11 (i.e., CFC-11, trichlorofluoromethane), R-245fa (i.e. HFC-245fa, 1,1,1,3,3-pentafluoropropane), R-114 (i.e., CFC-114, 1,2-dichloro-1,1,2,2-tetrafluoroethane), R-236fa (i.e., HFC-236a, 1,1,1,3,3,3-hexafluoropropane), R-236ea (i.e., HFC-236ea, 1,1,1,2,3,3-hexafluoropropane), R-124 (i.e., HCFC-124, 2-chloro-1,1,1,2-tetrafluoroethane), among others.

In some embodiments, the composition provided herein may be useful as refrigerants and provide at least comparable cooling performance (i.e., cooling capacity and energy efficiency) as the refrigerant for which a replacement is being sought. Additionally, the compositions of the present invention may provide heating performance (i.e., heating capacity and energy efficiency) comparable to a refrigerant being replaced.

In some embodiments the present application provides a method for recharging a heat transfer system that contains a refrigerant to be replaced and a lubricant, said method comprising removing the refrigerant to be replaced from the heat transfer system while retaining a substantial portion of the lubricant in said system and introducing one of compositions of the present invention to the heat transfer system. In some embodiments, the lubricant in the system is partially replaced (e.g., replace a portion of the mineral oil lubricant used with HCFC-123 with a POE lubricant).

In some embodiments, the compositions of the present invention may be used to top-off a refrigerant charge in a chiller. For example, if a chiller using HCFC-123 has diminished performance due to leakage of refrigerant, the compositions provided herein may be added to bring performance back up to specification.

The present application further provides a heat exchange system containing any of the compositions provided herein, wherein said system is selected from the group consisting of air conditioners, freezers, refrigerators, heat pumps, water chillers, flooded evaporator chillers, direct expansion chillers, walk-in coolers, heat pumps, mobile refrigerators, mobile air conditioning units, and systems having combinations thereof. Additionally, the compositions of the invention may be useful in secondary loop systems wherein these compositions serve as the primary refrigerant thus providing cooling to a secondary heat transfer fluid that thereby cools a remote location.

Vapor-compression refrigeration, air-conditioning, or heat pump systems include an evaporator, a compressor, a condenser, and an expansion device. A vapor-compression cycle re-uses refrigerant in multiple steps producing a cooling effect in one step and a heating effect in a different step. The cycle can be described simply as follows: Liquid refrigerant enters an evaporator through an expansion device, and the liquid refrigerant boils in the evaporator, by withdrawing heat from the environment, at a low temperature to form a vapor and produce cooling. The low-pressure vapor enters a compressor where the vapor is compressed to raise its pressure and temperature. The higher-pressure (compressed) vapor refrigerant then enters the condenser in which the refrigerant condenses and discharges its heat to the environment. The refrigerant returns to the expansion device through which the liquid expands from the higher-pressure level in the condenser to the low-pressure level in the evaporator, thus repeating the cycle.

The present application further provides foam expansion agent compositions comprising a composition of the invention for use in preparing foams. In some embodiments, the present application provides foamable compositions, including but not limited to, thermoset (e.g., polyurethane, polyisocyanurate, or phenolic) foam compositions, thermoplastic (e.g., polystyrene, polyethylene, or polypropylene) foam compositions and methods of preparing foams. In some embodiments, one or more of the present compositions may be included as a foam expansion agent in the foamable compositions, wherein foamable composition may include one or more additional components capable of reacting and/or mixing and foaming under the proper conditions to form a foam or cellular structure.

The present application further provides a method of forming a foam comprising: (a) adding to a foamable composition a composition of the present invention; and (b) processing the foamable composition under conditions effective to form a foam.

The present application further provides the use of the compositions of the present invention as propellants in sprayable compositions. Additionally, the present application provides sprayable compositions of the invention. The active ingredient to be sprayed together with inert ingredients, solvents, and other materials may also be present in a sprayable composition. In some embodiments, the sprayable composition is an aerosol. The compositions of the invention can also be used to formulate a variety of industrial aerosols or other sprayable compositions such as contact cleaners, dusters, lubricant sprays, mold release sprays, insecticides, and the like, and consumer aerosols such as personal care products (e.g., hair sprays, deodorants, and perfumes), household products (e.g., waxes, polishes, pan sprays, room fresheners, and household insecticides), and automotive products (e.g., cleaners and polishers), as well as medicinal materials such as anti-asthma and anti-halitosis medications. Examples include, but are not limited to, metered dose inhalers (MDIs) for the treatment of asthma and other chronic obstructive pulmonary diseases and for delivery of medicaments to accessible mucous membranes or intranasally.

The present invention further provides a process for producing aerosol products comprising the step of adding a composition of the invention to a formulation to an aerosol container, wherein said composition of the invention functions as a propellant. Additionally, the present application further provides a process for producing aerosol products comprising the step of adding a composition of the invention to a barrier type aerosol package (e.g., a bag-in-a-can or piston can) wherein said composition of the invention is kept separated from other formulation ingredients in an aerosol container, and wherein said composition of the invention functions as a propellant. Additionally, the present application further provides a process for producing aerosol products comprising the step of adding only a composition of the invention to an aerosol package, wherein said composition functions as the active ingredient (e.g., a duster, or a cooling or freezing spray).

The present application further provides a process for converting heat from a heat source to mechanical energy, comprising heating a working fluid comprising a composition of the invention and thereafter expanding the heated working fluid. In the process, heating of the working fluid uses heat supplied from the heat source; and expanding of the heated working fluid generates mechanical energy as the pressure of the working fluid is lowered.

The process for converting heat may be a subcritical cycle, a trans-critical cycle, or a supercritical cycle. In a transcritical cycle, the working fluid is compressed to a pressure above its critical pressure prior to being heated, and then during expansion the working fluid pressure is reduced to below its critical pressure. In a super critical cycle, the working fluid remains above its critical pressure for the complete cycle (e.g., compression, heating, expansion and cooling).

Heat sources may include, for example, low pressure steam, industrial waste heat, solar energy, geothermal hot water, low-pressure geothermal steam (primary or secondary arrangements), or distributed power generation equipment utilizing fuel cells or prime movers such as turbines, microturbines, or internal combustion engines. One source of low-pressure steam could be the process known as a binary geothermal Rankine cycle. Large quantities of low-pressure steam can be found in numerous locations, such as in fossil fuel powered electrical generating power plants. Other sources of heat include waste heat recovered from gases exhausted from mobile internal combustion engines (e.g., truck or rail diesel engines or ships), waste heat from exhaust gases from stationary internal combustion engines (e.g., stationary diesel engine power generators), waste heat from fuel cells, heat available at combined heating, cooling and power or district heating and cooling plants, waste heat from biomass fueled engines, heat from natural gas or methane gas burners or methane-fired boilers or methane fuel cells (e.g., at distributed power generation facilities) operated with methane from various sources including biogas, landfill gas and coal-bed methane, heat from combustion of bark and lignin at paper/pulp mills, heat from incinerators, heat from low pressure steam at conventional steam power plants (to drive "bottoming" Rankine cycles), and geothermal heat.

In some embodiments, the process of converting heat is performed using an organic Rankine power cycle. Heat available at relatively low temperatures compared to steam (inorganic) power cycles can be used to generate mechanical power through Rankine cycles using working fluids as described herein. In some embodiments, the working fluid is compressed prior to being heated. Compression may be provided by a pump which pumps working fluid to a heat transfer unit (e.g., a heat exchanger or an evaporator) where heat from the heat source is used to heat the working fluid.

The heated working fluid is then expanded, lowering its pressure. Mechanical energy is generated during the working fluid expansion using an expander. Examples of expanders include, but are not limited to, turbo or dynamic expanders, such as turbines, and positive displacement expanders, such as screw expanders, scroll expanders, and piston expanders. Examples of expanders also include rotary vane expanders.

Mechanical power can be used directly (e.g., to drive a compressor) or be converted to electrical power through the use of electrical power generators. In a power cycle where the working fluid is re-used, the expanded working fluid is cooled. Cooling may be accomplished in a working fluid cooling unit (e.g., a heat exchanger or a condenser). The cooled working fluid can then be used for repeated cycles (i.e., compression, heating, expansion, etc.). The same pump used for compression may be used for transferring the working fluid from the cooling stage.

The present application further provides a method for detecting a leak from a container comprising sampling the air in the vicinity of the container and detecting at least one additional compound of a composition provided herein with means for detecting the leak, wherein a composition of the present invention is contained inside the container. The term "in the vicinity of" refers to within 12 inches of the outside surface of the container. Alternatively, in the vicinity may be within 6 inches, within 3 inches or within one inch of the outside surface of the container.

A container may be any known container or system or apparatus that is filled with a composition of the inventor. A container may include, but is not limited to, a storage container, a transport container, an aerosol can, a fire extinguishing system, a chiller apparatus, a heat pump apparatus, heat transfer container, and a power cycle apparatus (e.g., an organic Rankine cycle system).

Means for detecting a leak may be performed using any known sensor designed to detect leaks. In particular, means for detecting the leak includes, but is not limited to, electrochemical, corona discharge, and mass spectroscopic leak detectors.

EXAMPLES

The invention will be described in greater detail by way of specific examples.

The following examples are offered for illustrative purposes, and are not intended to limit the invention in any manner.

Example 1. Vapor Phase Synthesis of Compositions Containing E-1336mzz & 1333azd

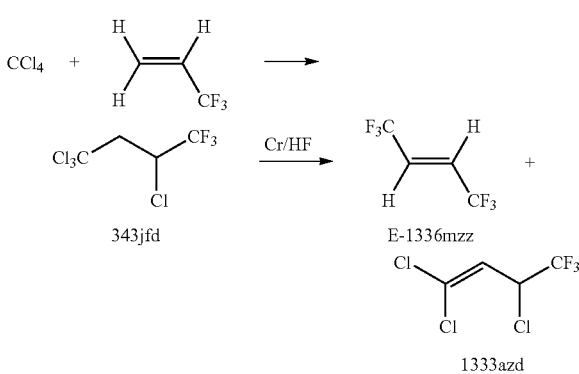

Step 1. 1,1,3-trichloro-4,4-trifluorobut-1-ene (343jfd)

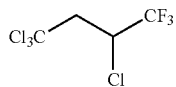

3,3,3-trifluoropropene (66 g, 0.68 mol) was added to the mixture of carbon tetrachloride (158 g, 1.0 mol), Fe powder (1.12 g, 0.02 mol) and tributylphosphate (2.66, 0.01 mol) in a 400 mL hastelloy reactor. The reactor was heated up to 110° C. for 3 hours. 217 g mixture was transferred to a container and analyzed by GC (100% TFP conversion, 88% selectivity to 343jfd). The same reaction was repeated twice and all three batches of the material were combined. The subsequent fractionation provided 299 g 98.5% pure 2,4,4,4-tetrachloro-1,1,1-trifluorobutane (343jfd). b.p. 92-94° C./140 torr; $^1$H NMR (CDCl$_3$, 400 MHz) δ 4.52 (1H, q-d-d, J1=J2=6.9 Hz, J3=1.8 Hz), 3.44 ($^1$H, d-d, J1=16.0 Hz, J2=1.9 Hz), 3.26 (1H, d-d, J1=16.0 Hz, J2=7.6 Hz). $^{19}$F NMR (CDCl$_3$, 376 MHz) δ -74.85 (3F, d, J=6.9 Hz). MS (E): 213 (M$^+$-Cl)

Step 2. (E)-1,1,1,4,4,4-hexafluorobut-2-ene (E-1336mzz) & 1,1,3-trichloro-4,4-trifluorobut-1-ene (1333azd)

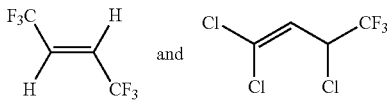

An Inconel® pipe (0.5 inch outer diameter, 10 inch length, 0.35 inch wall thickness) was filled with 6 cc of Cr$_2$O$_3$ catalyst (Newport Cr). The catalyst was activated with HF at 300° C., and the reaction was performed in the vapor phase at 300° C. 1,1,3-trichloro-4,4-trifluorobut-1-ene (343jfd) was fed into the reactor at 0.15 mL/h or 0.3 mL/h via a vaporizer controlled at 180° C., and the HF feed was 8.14 sccm or 17.23 sccm. The contact time was 18 seconds or 9 seconds. The pressure of the reaction was between 0 to 150 psig (0 to 1.03 MPa). The effluent of the reactor was analyzed using an Agilent® 7890 GC/5971 MS and showed E-1336mzz selectivity greater than 85 mol %, with the mixture containing 1333azd, 1336mt, 346mdf, 1335lzz, Z-1336mzz, 356mff, and 1326mxz.

Example 2. Vapor Phase Synthesis of 1333azd

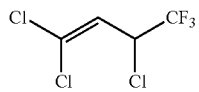

An Inconel® pipe (0.5 inch outer diameter, 10 inch length, 0.35 in wall thickness) was filled with 2 cc of Cr$_2$O$_3$ catalyst (Newport Cr). The catalyst was activated with HF at 300° C., and the reaction was performed in the vapor phase at 175° C. 2,4,4,4-tetrachloro-1,1,1-trifluorobutane (343jfd; Example 1, Step 1) was fed into the reactor at 0.25 mL/h via a vaporizer controlled at 180° C., and the contact time was 18 seconds. The pressure of the reaction was between 0 to 150 psig (0 to 1.03 MPa). The resulting product was collected in a cylinder and NMR showed 100% conversion of 343jfd with greater than 95% selectivity towards 1333azd. $^{19}$F NMR (470 MHz, CDCl$_3$): δ -74.05 (3F, d, 3JF-H=6.2 Hz). $^1$H NMR (500 MHz, CDCl$_3$): δ 6.06 (1H, CH, d, 3JH-H=9.9 Hz), 4.99 (1H, CHCl, dq, 3JH-H=9.9 Hz, 3JH-F=6.2 Hz). MS (EI): 212 (M$^+$), 214 (M$^+$).

Example 2. Liquid Phase Synthesis of 1333azd

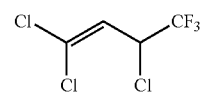

A 250 mL three-neck round bottomed flask was charged with 6 g (0.036 mol) of FeCl$_3$. The flask was placed in fume hood and equipped with thermocouple well, dry-ice condenser connected to water scrubber, magnetic stir bar, and 100 mL (155 g, 0.62 mol) 343jfd was added to the flask. The reaction mixture was heated to about 80° C. at which time a visible evolution off HCl was observed. Over period of about 10 h the reaction temperature slowly was increased from 80° C. to 110° C. The reaction progress was monitored by GC and once the conversion of starting material was >98%, the reaction mixture was poured into 500 mL of water, the organic layer was separated, washed with water (300 mL), separated, dried over MgSO$_4$, filtered, and the crude material (135 g) was distilled to give 105 g (79.5%) of 1,1,3-trichloro-4,4-trifluorobut-1-ene (1333azd; b.p. 115.2° C.-115.6° C.) and 5.6 g of residue, containing residual HCFO-1333azd and starting material (major components). The purity of isolated 1333azd was >99% (NMR and GC).

Example 3. Synthesis of E-1336mzz

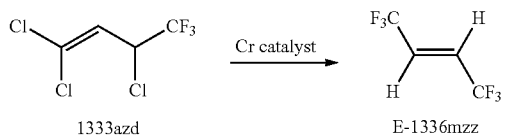 [SMILES: FC(F)(F)C(Cl)C=C(Cl)Cl ; FC(F)(F)/C=C/C(F)(F)F]

An Inconel® pipe (0.5 inch outer diameter, 10 inch length, 0.35 in wall thickness) is filled with 6 cc of Cr$_2$O$_3$ catalyst (Newport Cr). The catalyst is activated with HF at 300° C., and the reaction is performed in the vapor phase at 275° C. 1,1,3-trichloro-4,4-trifluorobut-1-ene (1333azd) is fed into the reactor at 0.14 mL/h or 0.29 mL/h via a vaporizer controlled at 150° C. and the HF feed is 8.14 sccm or 17.23 sccm. The contact time is 18 seconds or 9 seconds. The pressure of the reaction is between 0 to 150 psig (0 to 1.03 MPa). The effluent of the reactor is analyzed online using an Agilent® 7890 GC/5971 MS and shows E-1336mzz selectivity greater than 90 mol %, and the rest of the mixture contains 1333azd, 1336mt, 346mdf, 1335lzz, Z-1336mzz, 356mff, and 1326mxz.

OTHER EMBODIMENTS

1. In some embodiments, the present application provides a process of preparing 1,1,3-trichloro-4,4,4-trifluorobut-1-ene, comprising:

i) heating 2,4,4,4-tetrachloro-1,1,1-trifluorobutane in the presence of a metal catalyst to form the 1,1,3-trichloro-4,4,4-trifluorobut-1-ene.

2. The process of embodiment 1, wherein said heating is conducted in the absence of HF.

3. The process of embodiment 1 or 2, comprising a further step of (ii) substantially isolating 1,1,3-trichloro-4,4,4-trifluorobut-1-ene.

4. The process of any one of embodiments 1 to 3, wherein the metal catalyst is a transition metal oxide catalyst or a transition metal halide catalyst.

5. The process of embodiment 4, wherein the transition metal oxide catalyst is selected from chromium oxide, chromium oxide on carbon, chromium chloride, and chromium chloride on carbon.

6. The process of embodiment 4, wherein the transition metal oxide catalyst is chromium oxide.

7. The process of embodiment 4, wherein the transition metal oxide catalyst is chromium oxide on carbon.

8. The process of embodiment 7, wherein the process further comprises: a) contacting the chromium oxide on carbon with hydrogen fluoride prior to the reacting of step i) to form an activated chromium catalyst.

9. The process of embodiment 8, wherein the contacting of step a) is performed at a temperature of from about 280° C. to about 320° C.

10. The process of any one of embodiments 1 to 9, wherein the reacting of step i) is performed at a temperature of from about 150° C. to about 200° C.

11. The process of any one of embodiments 1 to 10, wherein the reacting is performed at a pressure of from about 0 psig to about 150 psig.

12. The process of any one of embodiments 1 to 11, wherein the process is a vapor phase process.

13. The process of embodiment 4, wherein the metal halide catalyst is an iron halide catalyst.

14. The process of embodiment 13, wherein the metal halide catalyst is iron (III) chloride.

15. The process of any one of embodiments 1 to 4, 13, and 14, wherein the reacting of step i) is performed at a temperature of from about 75° C. to about 115° C.

16. The process of any one of embodiments 1 to 4 and 13 to 15, wherein the process is a liquid phase process.

17. The process of any one of embodiments 1 to 16, wherein the process is performed in the absence of an additional solvent component.

18. The process of any one of embodiments 1 to 17, wherein the 1,1,3-trichloro-4,4,4-trifluorobut-1-ene is substantially isolated by distillation.

19. The process of any one of embodiments 1 to 18, wherein the 1,1,3-trichloro-4,4,4-trifluorobut-1-ene is isolated in greater than about 75% yield.

20. The process of any one of embodiments 1 to 19, wherein the 1,1,3-trichloro-4,4,4-trifluorobut-1-ene is isolated in greater than about 99% purity.

21. The process of any one of embodiments 1 to 20, further comprising: iii) heating the 1,1,3-trichloro-4,4,4-trifluorobut-1-ene in the presence of a second transition metal catalyst to form (E)-1,1,1,4,4,4-hexafluorobut-2-ene.

22. The process of embodiment 21, wherein the second transition metal oxide catalyst is chromium (III) oxide.

23. The process of any one of embodiments 1 to 22, wherein the 2,4,4,4-tetrachloro-1,1,1-trifluorobutane is prepared by a process comprising reacting 3,3,3-trifluoroprop-1-ene with carbon tetrachloride in the presence of a third transition metal catalyst and a tri($C_{1-6}$ alkyl) phosphate.

24. The process of embodiment 23, wherein the third transition metal catalyst is iron powder.

25. The process of embodiment 23 or 24, wherein the tri($C_{1-6}$ alkyl)phosphate is tributyl phosphate.

26. In some embodiments, the present application further provides a liquid phase process of preparing 1,1,3-trichloro-4,4,4-trifluorobut-1-ene, comprising: i) heating 2,4,4,4-tetrachloro-1,1,1-trifluorobutane in the presence of an aqueous base to form the 1,1,3-trichloro-4,4,4-trifluorobut-1-ene.

27. The process of embodiment 26, further comprising (ii) substantially isolating the 1,1,3-trichloro-4,4,4-trifluorobut-1-ene.

28. The process of embodiment 26 or 27, wherein the aqueous base is an aqueous hydroxide base.

29. The process of embodiment 26 or 27, wherein the aqueous base is aqueous sodium hydroxide or aqueous potassium hydroxide.

30. The process of any one of embodiments 26 to 29, further comprising: iii) heating the 1,1,3-trichloro-4,4,4-trifluorobut-1-ene in the presence of a transition metal catalyst to form (E)-1,1,1,4,4,4-hexafluorobut-2-ene.

31. The process of embodiment 30, wherein the transition metal catalyst is a chromium oxide catalyst.

32. The process of embodiment 30, wherein transition metal catalyst is chromium (III) oxide.

33. The process of embodiment 30, wherein the transition metal catalyst is chromium (III) oxide on carbon.

34. The process of embodiment 33, further comprising contacting the chromium (III) oxide on carbon with hydrogen fluoride to form an activated chromium (III) oxide on carbon catalyst prior to the heating of step iii).

35. In some embodiments, the present application further provides a vapor phase process of preparing 1,1,3-trichloro-4,4,4-trifluorobut-1-ene, comprising:

i) contacting chromium (III) oxide with hydrogen fluoride at a temperature of from about 280° C. to about 320° C. to form an activated chromium (III) catalyst; and ii) heating 2,4,4,4-tetrachloro-1,1,1-trifluorobutane in the presence of the activated chromium (III) oxide catalyst at a temperature of from about 150° C. to about 200° C. and at a pressure of from about 0 psig to 150 psig to form the 1,1,3-trichloro-4,4,4-trifluorobut-1-ene.

36. The process of embodiment 35, further comprising substantially isolating the 1,1,3-trichloro-4,4,4-trifluorobut-1-ene.

37. In some embodiments, the present application further provides a liquid phase process of preparing 1,1,3-trichloro-4,4,4-trifluorobut-1-ene, comprising:

i) heating 2,4,4,4-tetrachloro-1,1,1-trifluorobutane in the presence of iron (III) chloride at a temperature of from about 75° C. to about 115° C. to form the 1,1,3-trichloro-4,4,4-trifluorobut-1-ene.

38. The process of embodiment 37, further comprising substantially isolating the 1,1,3-trichloro-4,4,4-trifluorobut-1-ene 39. The process of any one of embodiments 35 to 38, wherein the heating of step ii) is conducted in the absence of hydrogen fluoride.

40. In some embodiments, the present application further provides a composition, comprising:

(E)-1,1,1,4,4,4-hexafluorobut-2-ene;

(Z)-1,1,1,4,4,4-hexafluorobut-2-ene;

3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene;

which is prepared according to a process comprising heating 2,4,4,4-tetrachloro-1,1,1-trifluorobutane in the presence of a metal catalyst to form the composition.

41. The composition of embodiment 40, wherein the heating is conducted in the presence of hydrogen fluoride.

42. The composition of embodiment 40 or 41, wherein the metal catalyst is a transition metal oxide catalyst or a transition metal halide catalyst.

43. The composition of embodiment 40 or 41, wherein the metal catalyst is chromium oxide on carbon.

44. The composition of any one of embodiments 41 to 43, wherein the process further comprises contacting the chromium oxide on carbon with the hydrogen fluoride to form an activated chromium catalyst prior to heating the 2,4,4,4-tetrachloro-1,1,1-trifluorobutane.

45. The composition of any one of embodiments 40 to 44, wherein the process is a vapor phase process.

46. In some embodiments, the present application further provides a composition, comprising:
(E)-1,1,1,4,4,4-hexafluorobut-2-ene;
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene;

which is prepared according to a process comprising:
i) heating 2,4,4,4-tetrachloro-1,1,1-trifluorobutane in the presence of a first metal catalyst to form a first mixture comprising 1,1,3-trichloro-4,4,4-trifluorobut-1-ene;
ii) heating the 1,1,3-trichloro-4,4,4-trifluorobut-1-ene in the presence of a transition metal catalyst to form the composition.

47. The process of embodiment 46, wherein step i) is performed in the presence of hydrogen fluoride.

48. The process of embodiment 46 or 47, wherein step ii) is performed in the presence of hydrogen fluoride.

49. The process of embodiment 46, wherein step i) is performed in the absence of hydrogen fluoride.

50. The process of embodiment 49, wherein step ii) is performed in the presence of hydrogen fluoride.

51. The composition of any one of embodiments 46 to 50, wherein the process of preparing the composition further comprises substantially isolating the 1,1,3-trichloro-4,4,4-trifluorobut-1-ene prior to the heating of step ii).

52. The composition of any one of embodiments 46 to 51, wherein the process of preparing the composition further comprises substantially isolating the composition.

53. The composition of any one of embodiments 46 to 52, wherein the composition comprises greater than about 99 mole percent (E)-1,1,1,4,4,4-hexafluorobut-2-ene.

54. In some embodiments, the present application further provides a composition, comprising:
2,4,4,4-tetrachloro-1,1,1-trifluorobutane;
1,1,1-trichloro-4,4,4-trifluorobutane; and
1,1,1-trichloro-2-(chloromethyl)-3,3,3-trifluoropropane;

which is prepared according to a process comprising:
i) reacting 3,3,3-trifluoroprop-1-ene with carbon tetrachloride in the presence of a transition metal catalyst and a tri($C_{1-6}$ alkyl) phosphate in the presence of a transition metal catalyst to form the composition; and
ii) substantially isolating the composition.

55. The composition of embodiment 54, wherein the composition comprises greater than about 99 mole percent 2,4,4,4-tetrachloro-1,1,1-trifluorobutane.

56. In some embodiments, the present application further provides a composition, comprising:
(E)-1,1,1,4,4,4-hexafluorobut-2-ene;
(Z)-1,1,1,4,4,4-hexafluorobut-2-ene;
3,3,3-trifluoro-2-(trifluoromethyl)prop-1-ene;
2-chloro-1,1,1,4,4,4-hexafluorobut-2-ene;
1,1,1,4,4,4-hexafluorobutane; and
1-chloro-1,1,4,4,4-pentafluorobut-2-ene;

wherein the composition is prepared according to a process described herein.

57. In some embodiments, the present application further provides a composition, comprising:
2,4,4,4-tetrachloro-1,1,1-trifluorobutane;
1,1,1-trichloro-4,4,4-trifluorobutane; and
1,1,1-trichloro-2-(chloromethyl)-3,3,3-trifluoropropane;

wherein the composition is prepared according to a process described herein.

58. The composition of any one of embodiments 40 to 57, wherein the process of preparing the composition further comprises substantially isolating the composition.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

What is claimed is:

1. A process of preparing 1,1,3-trichloro-4,4,4-trifluorobut-1-ene, comprising:
   i) heating 2,4,4,4-tetrachloro-1,1,1-trifluorobutane in the presence of a metal catalyst to form the 1,1,3-trichloro-4,4,4-trifluorobut-1-ene, wherein said heating is conducted in the absence of hydrogen fluoride; and wherein the product comprises said 1,1,3-trichloro-4,4,4-trifluorobut-1-ene.

2. The process of claim 1, comprising a further step of (ii) substantially isolating 1,1,3-trichloro-4,4,4-trifluorobut-1-ene.

3. The process of claim 1, wherein the metal catalyst is a transition metal oxide catalyst selected from chromium oxide, chromium oxide on carbon, chromium chloride, and chromium chloride on carbon and wherein the process is a vapor phase process.

4. The process of claim 3, wherein the process further comprises: contacting the chromium oxide on carbon with hydrogen fluoride prior to the heating of step i) to form an activated chromium catalyst.

5. The process of claim 4, wherein the contacting of the chromium oxide on carbon with hydrogen fluoride is performed at a temperature of from about 280° C. to about 320° C.

6. The process of claim 4, wherein the heating of step i) is performed at a temperature of from about 150° C. to about 200° C.

7. The process of claim 4, wherein the heating of step i) is performed at a pressure of from about 0 psig to about 150 psig.

8. The process of claim 1, wherein the metal catalyst is a metal halide catalyst, which is an iron halide catalyst and wherein the process is a liquid phase process.

9. The process of claim 8, wherein the heating of step i) is performed at a temperature of from about 75° C. to about 115° C.

10. The process of claim 8, wherein the 1,1,3-trichloro-4,4,4-trifluorobut-1-ene is substantially isolated by distillation.

11. The process of claim 10, wherein the 1,1,3-trichloro-4,4,4-trifluorobut-1-ene is isolated in greater than about 99% purity.

12. The process of claim 1, further comprising:
 iii) heating the 1,1,3-trichloro-4,4,4-trifluorobut-1-ene in the presence of a second transition metal catalyst to form (E)-1,1,1,4,4,4-hexafluorobut-2-ene.

13. The process of claim 12, wherein the second transition metal oxide catalyst is chromium (III) oxide.

\* \* \* \* \*